United States Patent
Colignon et al.

[11] Patent Number: 5,382,677
[45] Date of Patent: Jan. 17, 1995

[54] PROCESS FOR THE PRODUCTION OF HIGHLY CONCENTRATED PASTES OF α-SULFOFATTY ACID ALKYL ESTER ALKALI METAL SALTS

[75] Inventors: Dietmar Colignon, Erkrath; Erich Dorra, Duesseldorf; Guenter Panthel, Haan; Wolfgang Schmidt, Monheim; Norbert Wrede, Duesseldorf, all of Germany

[73] Assignee: Henkel Kommanditgesellschaft auf Aktien, Duesseldorf, Germany

[21] Appl. No.: 949,511

[22] PCT Filed: May 21, 1991

[86] PCT No.: PCT/EP91/00939
§ 371 Date: Nov. 24, 1992
§ 102(e) Date: Nov. 24, 1992

[87] PCT Pub. No.: WO91/18870
PCT Pub. Date: Dec. 12, 1991

[30] Foreign Application Priority Data
May 30, 1990 [DE] Germany ............... 4017468

[51] Int. Cl.$^6$ ............................ C07C 303/32
[52] U.S. Cl. ........................ 554/98; 554/85; 554/96; 554/97
[58] Field of Search .............. 554/97, 98, 85, 96

[56] References Cited

U.S. PATENT DOCUMENTS

| | | | |
|---|---|---|---|
| 3,251,868 | 5/1966 | Stein et al. | 260/400 |
| 4,102,911 | 7/1978 | Majimu et al. | 554/98 |
| 4,668,438 | 5/1987 | Pierr et al. | 260/400 |

FOREIGN PATENT DOCUMENTS

| | | | |
|---|---|---|---|
| 401925 | 5/1990 | Australia | 534/97 |
| 0182118 | 5/1986 | European Pat. Off. | |
| 0222237 | 5/1987 | European Pat. Off. | |
| 3123681 | 3/1982 | Germany | |
| 3334517 | 4/1984 | Germany | |
| 3305430 | 8/1984 | Germany | |
| 3432324 | 3/1986 | Germany | |
| 3538910 | 5/1987 | Germany | |

Primary Examiner—José G. Dees
Assistant Examiner—D. D. Carr
Attorney, Agent, or Firm—Wayne C. Jaeschke; John E. Drach; Henry E. Millson, Jr.

[57] ABSTRACT

In the production of highly concentrated pastes of α-sulfofatty acid alkyl ester alkali metal salts by reaction of fatty acid alkyl esters with gaseous SO$_3$, subsequent after-reaction in liquid phase and neutralization with aqueous alkali hydroxide solutions, the sulfonation product and aqueous alkali metal hydroxide solution are introduced during neutralization into an aqueous phase initially containing at least 55% by weight washing-active substance at a pH value in the range from 2 to 8 and washing-active substance contents of 60 to 70% by weight are established.

20 Claims, 1 Drawing Sheet

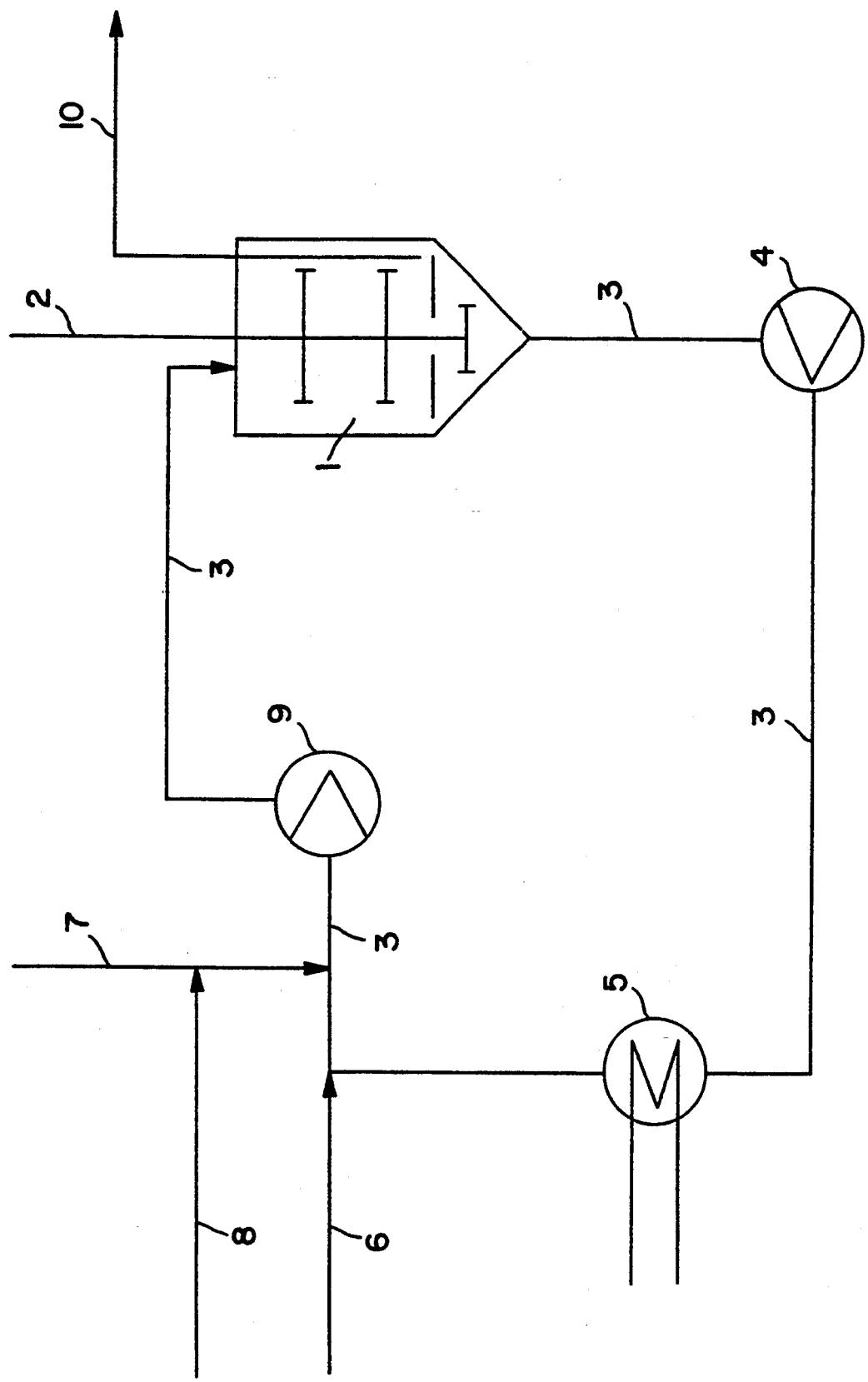

PROCESS FOR THE PRODUCTION OF HIGHLY CONCENTRATED PASTES OF α-SULFOFATTY ACID ALKYL ESTER ALKALI METAL SALTS

BACKGROUND OF THE INVENTION

1. Field of the Invention

This invention relates to a process for the production of free-flowing pastes of α-sulfofatty acid alkyl ester alkali metal salts containing 60 to 70% by weight washing-active substance, in which acidic α-sulfofatty acid alkyl esters are neutralized with aqueous alkali metal hydroxide solutions under defined pH conditions. In the context of the present invention, washing-active substance (WAS) is understood to be the sum total of α-sulfofatty acid alkyl ester alkali metal salt and the α-sulfofatty acid dialkali metal salt—always present as a secondary product—in the neutralized α-sulfofatty acid ester.

2. Statement of Related Art

α-Sulfofatty acid alkyl ester alkali metal salts are acquiring increasing significance as surfactants for detergents and cleaning preparations based on renewable natural raw materials. In known processes, the α-sulfofatty acid alkyl ester alkali metal salts are obtained in the form of aqueous solutions or pastes by neutralization of α-sulfofatty acid alkyl esters which may be synthesized reaction of lower fatty acid alkyl esters with gaseous $SO_3$. In the final analysis, the basis for the production of the α-sulfofatty acid alkyl ester alkali metal salts are fats and oils of natural origin from which the lower fatty acid alkyl esters are obtained by lipolysis and subsequent esterification of the free fatty acids with lower alkanols or by transesterification of the natural triglycerides with lower alkanols. In both reactions, methanol is preferably used as the lower alkanol. The lower fatty acid alkyl esters are mixtures in which $C_{6-22}$ fatty acid residues occur, the chain length distribution being dependent on the origin of the natural fats or oils. In many cases, these fatty acid mixtures are not used for the synthesis as such, but rather in the form of certain fractions. Sulfonation of the fatty acid ester mixtures with gaseous $SO_3$ gives acidic α-sulfofatty acid alkyl esters which are converted into aqueous pastes of α-sulfofatty acid alkyl ester alkali metal salts by neutralization to a pH value of 6 to 8. The crude α-sulfofatty acid alkyl esters and their alkali metal salts are more or less colored products which generally have to be treated with typical bleaches, such as hydrogen peroxide or alkali metal hypochlorite, before and/or after neutralization.

One particular difficulty involved in the production and handling of aqueous α-sulfofatty acid alkyl ester alkali metal salt pastes arises out of their viscosity behavior in dependence upon the solids concentration. In aqueous compositions, the α-sulfofatty acid alkyl ester alkali metal salts produced by conventional industrial processes (hereinafter also referred to in short as ester sulfonates) only form solutions or suspensions of such low viscosity that they flow sufficiently freely to guarantee uninterrupted completion of industrial processes at WAS contents of up to about 40% and then again beyond WAS contents of around 55%. In the intermediate concentration range, i.e. at WAS contents of around 40 to 55% by weight, the aqueous ester sulfonate compositions show extremely high viscosity values, assuming the form of more or less solid gels which can neither be stirred nor pumped. In addition, the lower and upper limits of the individual viscosity maxima can vary by ±5% by weigh solids content. As a result of this particular concentration/viscosity behavior, ester sulfonate pastes having WAS contents above 35 to 40% by weight cannot be obtained simply by neutralization of the acidic α-sulfofatty acid alkyl esters with the calculated quantity of aqueous alkali metal hydroxide solutions. After the lower limit to the viscosity maximum has been exceeded, the reacting mixture loses its stirrability and miscibility. The lack of stirrability and miscibility prevents adequate and rapid dissipation of the heat of neutralization. Local concentration and temperature peaks initiate unwanted secondary reactions, more particularly cleavage of the ester bonds present in the ester sulfonates, so that undesirably high concentrations of alkali metal disalts of the free α-sulfofatty acids are established in the end product. The subsequent processing of ester sulfonate pastes immobilized by the high increase in viscosity is of course also impaired to the point where it is no longer possible solely as a result of the fact that the aqueous compositions in question can no longer be poured or pumped.

The formation of disalts of the free α-sulfofatty acid alkyl esters is undesirable for several reasons. The disalts show only limited solubility in water and, in addition, have inadequate surface-active properties. Above all, however, disalts as secondary products in ester sulfonate pastes have a considerable viscosity-increasing effect.

There has been no shortage of attempts in the past to eliminate at least most of the unfavorable effects caused by the particular concentration/viscosity behavior of the ester sulfonates and the unwanted formation of α-sulfofatty acid disalts. Thus, it has been proposed to improve the flow behavior of aqueous ester sulfonate compositions by the addition of flow aids. According to DE-OS 33 05 430, aliphatic alcohols containing 8 to 40 carbon atoms and 1 to 6 hydroxyl groups, alkylphenols and adducts of up to 20 mol ethylene oxide and/or propylene oxide with the alcohols and alkyl phenols mentioned are used as viscosity regulators.

In connection with the unwanted formation of disalts during working up of the acidic α-sulfofatty acid alkyl esters, DE-OS 31 23 681 describes a process in which the neutralizing treatment is carried out in two steps. In the first step, neutralization is carried out to a pH value of 2.5 to 4 with a 15 to 50% by weight alkali metal hydroxide solution in the presence of a $C_{1-4}$ alcohol, preferably methanol, in a quantity of 5 to 20% by weight, based on the weight of the sulfonated product, before a final pH value of 6 to 7 is adjusted in the second neutralization step using a more heavily diluted alkali metal hydroxide solution. It is said to be possible by this process to reduce the disalt content of the ester sulfonate compositions to 5% by weight, based on washing-active substance, or less. A serious disadvantage of this process is obvious: the ester sulfonate pastes produced in this way contain considerable quantities of alcohol which are troublesome in the production of detergent mixtures by spray drying insofar as they can cause unwanted pluming. To limit the alcohol content of the end products, DE-OS 33 34 517 suggests carrying out the optional bleaching step and neutralization of the crude α-sulfofatty acid alkyl esters in the presence of such a quantity of a lower alcohol that an aqueous slurry containing 30 to 40% by weight and, based on the weight of the α-sulfofatty acid ester salt, 5 to 15% by weight of a lower alcohol sulfate and 8 to 40% by weight of the lower alcohol is obtained. Finally, the aqueous slurry is said to be concentrated to such an extent that it contains 40 to 65% by weight α-sulfofatty acid ester salt, 2 to 10% by weight lower alcohol sulfate and at most 2% by weight lower alcohol.

According to DE-OS 34 32 324, the disalt content of α-sulfofatty acid alkyl ester alkali metal salt pastes can be controlled and reduced by subjecting the crude sulfonation product before treatment with an aqueous medium to a transesterification reaction in which at least 0.5 mol-equivalent alcohol, based on the $SO_3$ which is not used for the sulfonation, is used. According to DE-OS 35 38 910, sulfofatty acid alkyl ester salt pastes having solids contents above 35% by weight can be produced by subjecting the crude ester sulfonates to transesterification in accordance with DE-OS 34 32 324 and then establishing solids contents of more than 35% by weight in the aqueous pastes during subsequent working by neutralization with or without preliminary or subsequent bleaching.

Processes for the production of α-sulfofatty acid alkyl ester alkali metal salts in which lower alcohols are added during working up of the crude sulfonation products are attended by the disadvantage that they lead to pasty compositions which cannot be sufficiently lightened with the usual bleaches.

BRIEF DESCRIPTION OF THE DRAWING

FIG. 1 is a schematic representation of the neutralization process.

DESCRIPTION OF THE INVENTION

The problem addressed by the present invention was to find a process which would enable free-flowing and pumpable ester sulfonate pastes having WAS contents of 60 to 70% by weight to be obtained by direct neutralization of the acidic α-sulfofatty acid alkyl esters with aqueous alkali metal hydroxide solutions without any need for the addition of "foreign" substances, such as relatively long chain aliphatic mono- and polyalcohols and alkylene oxide adducts thereof, alkylphenols and alkylene oxide adducts thereof or short-chain alcohols. The teaching according to the invention is based on the surprising observation that this problem can be solved if, during neutralization, the acidic sulfonation product and the aqueous alkali metal hydroxide solution are introduced into an already present aqueous α-sulfofatty acid alkyl ester alkali metal salt paste and if, at the same time, provision is made to ensure that the pH value of the aqueous phase lies within a certain range.

The present invention relates to a process for the production of highly concentrated, readily bleachable pastes of α-sulfofatty acid alkyl ester alkali metal salts by reaction of fatty acid alkyl esters with gaseous $SO_3$, subsequent after-reaction in liquid phase and neutralization with aqueous alkali hydroxide solutions, in which the sulfonation product and aqueous alkali metal hydroxide solution are introduced during neutralization into an aqueous phase initially containing at least 55% by weight α-washing-active substance at a pH value in the range from 2 to 8 and washing-active substance contents of 60 to 70% by weight and preferably 60 to 65% by weight are established.

In one particular embodiment of the invention, the sulfonation product and the aqueous alkali metal hydroxide solution are introduced into an aqueous phase initially containing 60 to 70% by weight washing-active substance.

At the beginning of neutralization, the solutions containing washing-active substance are adjusted to a pH value in the range from 2 to 8.

In one preferred embodiment of the invention, a pH value in the range from 5 to 8 and preferably in the range from 5.5 to 7.5 is adjusted and maintained in the aqueous phase during the neutralization process.

The pH value of the aqueous phase is preferably maintained by variation of the feed rates of α-sulfofatty acid alkyl ester and aqueous alkali metal hydroxide solution. The neutralization of the α-sulfofatty acid alkyl ester is best carried out at temperatures below 95° C. and preferably at temperatures in the range from 60° to 90° C. Sodium hydroxide is preferably used as the neutralization base.

Neutralization of the acidic α-sulfofatty acid alkyl ester is best carried out in a neutralization loop of the type diagrammatically illustrated in FIG. 1. The predominant part of the aqueous phase is accommodated in the stirred tank 1 in which it is continuously stirred by the stirrer 2. Aqueous phase is continuously removed by the circulation pump 4 via the circulation pipe 3 and is cooled to the necessary extent in the cooler 5 provided to control the reaction temperature. The α-sulfofatty acid alkyl ester to be neutralized is introduced into the stream of the circulated aqueous phase through the pipe 6. Aqueous alkali metal hydroxide solution having a standard concentration, for example 50% by weight sodium hydroxide solution, is introduced into the circuit through the pipe 7. The concentration of the standard alkali metal hydroxide solution can be reduced to the particular value required before it is introduced into the product circuit by the introduction of water through the pipe 8. The mixture of acidic α-sulfofatty acid alkyl ester, alkali metal hydroxide solution and circulated aqueous phase then enters the mixer 9 for further homogenization and, from the mixer 9, is transported into the stirred tank 1 through the last section of the circulation pipe 3. The α-sulfofatty acid alkyl ester alkali metal salt paste formed during neutralization can be removed through the pipe 10. A neutralization loop of the type described in the foregoing may be made up exclusively of standard units, fittings and pipes. Known measuring and control methods for chemical processes may be used for the necessary monitoring of the pH value and the reaction temperature and for controlling the product and coolant flows.

The process according to the invention may be continuously carried out in the described neutralization loop by suitable control of the critical parameters. In the continuous embodiment of the process, α-sulfofatty acid alkyl ester sodium salt paste is removed through the pipe 10 at the same rate as sulfonation product and alkali metal hydroxide are introduced through the pipes 6 and 7, respectively.

The pastes containing at least 55% by weight washing-active substance which are used as the aqueous phase for carrying out the process may be prepared in the neutralization loop by introduction of acidic α-sulfofatty acid alkyl ester and the quantity of aqueous alkali metal hydroxide solution required for its neutralization into a predetermined quantity of water with pump-circulation of the aqueous phase at a pH value in the range from 2 to 8 and preferably in the range from 3 to 5 and at a temperature below 95° C. and preferably in the range from 60° to 90° C. until the desired content of washing-active substance is established in the aqueous phase.

In the context of the invention, fatty acid alkyl esters are understood to be lower alkyl esters of saturated fatty acids, more particularly esters of fatty acids containing 10 to 18 carbon atoms and saturated aliphatic alcohols containing 1 to 4 carbon atoms. Basically, individual fatty acid alkyl esters may be used as starting material. In general, however, ester mixtures of the type obtainable from fats and oils of natural origin either by ester cleavage and subsequent esterification with lower alkanols or by transesterification with lower alkanols by known methods are used as the starting material, the corresponding fatty acid methyl ester mixtures being preferred. If the fatty acid ester mixtures obtained in this way have relatively large percentage contents of esters of fatty acids containing less than 10 carbon atoms, these "head-fractionated fatty acid esters" are generally removed by distillation. Apart from the $CH_2$ group in the $\alpha$-position to the ester group, the fatty acid esters should not contain any sulfatable or sulfonatable groups. For this reason, hydroxyfatty acid esters or mixtures containing hydroxy-fatty acid esters are not suitable as starting materials. Fatty acid ester mixtures containing non-negligible quantities of esters of unsaturated fatty acids, more particularly esters having an iodine value above 5, are only suitable as starting materials after saturation of the double bonds in the course of hardening by hydrogenation using known methods. During the hydrogenation, the iodine values of the ester mixtures are preferably reduced to values of 0.2 and lower.

The fatty acid esters are sulfonated with gaseous $SO_3$ as the sulfonating agent at temperatures in the range from 30° to 80° C. The $SO_3$ is contacted with the fatty acid esters after dilution with air or nitrogen, preferably in the form of a gas mixture containing 1 to 10% by volume $SO_3$. The quantity of $SO_3$ is gauged in such a way that the molar ratio of fatty acid ester to $SO_3$ is in the range from 1:1.2 to 1:1.8. This reaction may be carried out in standard reactors suitable for the sulfonation of organic compounds, such as fatty alcohols, alkyl benzenes of olefins, or particularly in falling-film reactors or multistage cascades of stirred tank reactors.

The crude sulfonation product issuing from the sulfonation reactor still does not have the desired degree of sulfonation. For this reason, the crude reaction product is delivered immediately after sulfonation to a suitable apparatus in which it is subjected to a temperature-controlled after-reaction for 20 to 40 minutes and preferably for 25 to 35 minutes with mechanical agitation until the desired degree of sulfonation is reached. The apparatus required for this reaction step may consist of a standard reactor with a heating and cooling circuit, a standard temperature-controlled pipe coil or a standard cascade of stirred tanks. The after-reaction is carried out at temperatures of 60° to 100° C. The sulfonated product may be mechanically agitated during the after-reaction by stirring, by introduction of the product under pressure, by the installation of chicane-like baffles in the apparatus or, where a pipe coil is used, by generation of turbulent flow. The after-reaction of the sulfonated product may be controlled by suitable choice of the parameters mentioned, more particularly the reaction time, in such a way that a degree of sulfonation of at least 90% and preferably from 94 to 98% is reached.

Following the after-reaction, the aged sulfonation product is subjected to neutralization in accordance with the invention.

The ester sulfonate pastes obtained after neutralization are more or less heavily colored substances which have to be bleached before subsequent processing. Bleaching is carried out in known manner using typical bleaches, such as aqueous solutions of sodium hypochlorite or, preferably aqueous solutions of hydrogen peroxide. Bleaching with hydrogen peroxide is carried out at pH values in the acidic range and preferably at pH values above 5.

EXAMPLE

The starting material used was a technical palmitic/-stearic acid methyl ester (in % by weight according to chain length in the fatty acid part: 0.2 $C_{12}$; 1.2 $C_{14}$; 61.4 $C_{16}$; 0.9 $C_{17}$; 35.9 $C_{18}$; 0.4 $C_{20}$; average molecular weight 281.5; acid value 1.1; iodine value 0.1; saponification value 202.1). The fatty acid methyl ester was continuously sulfonated with an $SO_3$/air mixture (5% by volume $SO_3$) in a molar ratio of 1:1.25 in a standard falling-film reactor at a temperature of 80° C. The resulting reaction mixture was subjected to an after reaction in a holding-time cascade of four stirred tanks with a holding time of 25 minutes. Thereafter the acid value of the sulfonation product was 198. The degree of sulfonation was 96%.

1,448 kg of an ester sulfonate paste having a WAS content of 62.5% by weight (52.0% by weight $\alpha$-sulfofatty acid methyl ester sodium salt and 10.5% by weight $\alpha$-sulfofatty acid disodium salt; pH 7.5) were introduced into a neutralization loop of the described type and then pump-circulated as the aqueous phase. The above-described, aged sulfonation product and 25% by weight aqueous sodium hydroxide solution were fed into the circulated aqueous phase at such a rate that a pH value of 7.5 was maintained in the aqueous phase. 0.53 kg 25% sodium hydroxide solution were introduced into the neutralization circuit per kg sulfonation product. After the aqueous phase had been heated to around 75° C. by the heat of neutralization released, the reaction temperature was kept at that value by means of the cooler. From this moment on, neutralized product was removed from the stirred tank at the same rate as sulfonation product and sodium hydroxide solution were introduced into the neutralization circuit. In this way, the neutralization circuit was kept in the steady state for several days. The aqueous phase could readily be stirred and pumped throughout the entire period.

The $\alpha$-sulfofatty acid methyl ester sodium salt paste continuously run off had a WAS content of 62.5±2.5% by weight. The composition of the washing-active substance accorded with that of the paste initially used as the aqueous paste within a certain range of variation.

The $\alpha$-sulfofatty acid methyl ester sodium salt paste originally used as the aqueous paste had been obtained as follows:

467 kg water were introduced into and pump-circulated in the described neutralization loop. 948 kg of the aged sulfonation product described above and 250 kg 50% by weight sodium hydroxide solution were initially fed into the circuit of the aqueous phase at such a rate that a pH value of 4.5 to 5.5 was maintained in the aqueous phase. When the WAS content of the aqueous phase had reached 55% by weight, the inflow rates of the sulfonation product and the sodium hydroxide solution were adjusted in such a way that the pH value in the aqueous phase was 6. After the entire acidic sulfonation product had been introduced into the neutralization circuit, the pH value of the aqueous phase was increased to 7.5 by addition of the remaining sodium hydroxide solution. Throughout the neutralization process, the reaction temperature was kept at 70° to 85° C.

What is claimed is:

1. A process for the production of highly concentrated, readily bleachable paste of an α-sulfofatty acid alkyl ester alkali metal salt which comprises: (1) contacting a fatty acid alkyl ester with gaseous sulfur trioxide to form a partially sulfonated product; (2) maintaining said partially sulfonated product at a temperature of from about 60° C. to about 100° C. for a time to form a sulfonated product having a degree of sulfonation of at least 90%; (3) neutralizing said sulfonated product by introducing the sulfonated product and an aqueous alkali metal hydroxide solution into an aqueous phase comprising at least 55% by weight washing-active substance while maintaining a pH of from about 2 to about 8 to form a α-sulfofatty acid alkyl ester alkali metal salt paste comprised of from about 60% to about 70% by weight washing-active substance.

2. The process of claim 1 wherein the pH of said aqueous phase in step (3) is maintained in the range of from about 5 to about 8 until a washing-active substance of from about 60% to about 65% by weight is achieved.

3. The process of claim 1 wherein said pH in step (3) is maintained in the range of from about 5.5 to about 7.5 until a washing-active substance of from about 60% to about 65% by weight is achieved.

4. The process of claim 1 wherein step (3) is carried out below about 95° C.

5. The process of claim 6 wherein step (3) is carried out at a temperature of from about 60° C. to about 90° C.

6. The process of claim 1 wherein in step (1) said fatty acid alkyl ester is a methyl ester.

7. the process of claim 6 wherein said fatty acid alkyl ester is a mixture of fatty acid methyl esters obtained by transesterification of natural fats or oils with methanol.

8. The process of claim 1 wherein in step (1) sulfur trioxide is part of a mixture comprised of up to 10% by volume sulfur trioxide and the remainder air or up to 10% by volume sulfur trioxide and the remainder nitrogen.

9. The process of claim 8 wherein the molar ratio of sulfur trioxide to fatty acid alkyl ester is from about 1.2/1.0 to about 1.8/1.0.

10. The process of claim 9 wherein the molar ratio of sulfur trioxide to fatty acid alkyl ester is about 1.2/1.0.

11. The process of claim 1 wherein step (1) is carried out in a falling film reactor or a multiple-stage sulfonation cascade.

12. The process of claim 1 wherein the degree of sulfonation in step (2) is from about 94% to about 98%.

13. The process of claim 1 further comprising the step of bleaching said α-sulfofatty acid alkyl ester alkali metal salt paste with a bleaching agent.

14. The process of claim 13 wherein said bleaching agent is hydrogen peroxide.

15. The process of claim 14 wherein said bleaching step is carried out at a pH above 5.0.

16. The process of claim 1 wherein step (2) is carried out in a reaction zone selected from the group consisting of a heating and cooling circuit, a temperature-controlled pipe coil, and a cascade of stirred-tank reactors.

17. The process of claim 16 wherein the reaction mixture in said reaction zone is mechanically agitated by stirring, by introduction of the reaction mixture into said zone under pressure, or by turbulent flow in said pipe coil.

18. The process of claim 1 wherein step (1) is carried out at a temperature of from about 30° to about 80° C.; and step (2) is carried out at a temperature in the range of from about 60° to about 100° C. for a period of from about 20 to about 40 minutes.

19. The process of claim 1 wherein step (1) is carried out at a temperature of from about 30° to about 80° C. and the molar ratio of sulfur trioxide to fatty acid alkyl ester is from 1.2/1.0 to 1.8/1.0; step (2) is carried out at a temperature in the range of from about 60° to about 100° C. for a period of from about 20 to about 40 minutes; the pH of the aqueous phase in step (3) is maintained in the range of from about 5 to about 8, and step (3) is carried out at a temperature of from about 60° to about 90° C.

20. The process of claim 19 wherein in step (1) the fatty acid alkyl ester is a mixture of fatty acid methyl esters obtained by transesterification of natural fats or oils with methanol.

* * * * *